United States Patent [19]

Kureshy et al.

[11] Patent Number: 5,207,987
[45] Date of Patent: May 4, 1993

[54] TEMPERATURE CONTROLLED CHAMBER FOR DIAGNOSTIC ANALYZER

[75] Inventors: Fareed Kureshy, Westwood; Shailendra Singh; Gary L. Webber, both of Sharon, all of Mass.

[73] Assignee: PB Diagnostic Systems Inc., Westwood, Mass.

[21] Appl. No.: 526,048

[22] Filed: May 21, 1990

[51] Int. Cl.$^5$ .................. G01N 21/13; C12M 1/38
[52] U.S. Cl. ..................... 422/67; 422/64; 422/109; 435/290; 435/291; 435/809; 436/48; 436/50; 219/388
[58] Field of Search .............. 219/400, 388-389; 422/64-67, 72, 109; 436/45, 47, 48, 50; 435/290-291, 809

[56] References Cited

U.S. PATENT DOCUMENTS

| | | | |
|---|---|---|---|
| 3,549,330 | 12/1970 | Jungner et al. | 23/259 |
| 3,574,064 | 5/1971 | Binnings et al. | 195/127 |
| 3,863,049 | 1/1975 | Hinmann | 219/389 |
| 3,916,152 | 10/1975 | Hinman | 219/389 |
| 3,969,079 | 7/1976 | Catarious et al. | 356/246 |
| 4,219,529 | 8/1980 | Tersteeg et al. | 422/65 |
| 4,224,032 | 9/1980 | Glover et al. | 23/230 |
| 4,276,258 | 6/1981 | Ginsberg et al. | 422/67 |
| 4,296,069 | 10/1981 | Smith et al. | 422/64 |
| 4,298,571 | 11/1981 | DiFulvio et al. | 422/65 |
| 4,303,611 | 12/1981 | Jessop | 422/67 |
| 4,406,547 | 9/1983 | Aihara | 422/64 |
| 4,497,774 | 2/1985 | Scordato | 422/67 |
| 4,539,296 | 9/1985 | Manabe | 436/47 |
| 4,568,519 | 2/1986 | Hamilton et al. | 422/64 |
| 4,584,275 | 4/1986 | Okano | 435/291 |
| 4,652,127 | 3/1987 | Ekholm et al. | 356/246 |
| 4,670,219 | 6/1987 | Nelson et al. | 422/67 |
| 4,699,766 | 10/1987 | Yamashita | 422/67 |
| 4,939,095 | 7/1990 | Yokotani | 422/67 |
| 5,051,238 | 9/1991 | Umetsu et al. | 422/67 |

FOREIGN PATENT DOCUMENTS 0151781 12/1984 European Pat. Off. .
61-013162 6/1984 Japan .

OTHER PUBLICATIONS

Omega Electric Heaters Handbook, 1989, pp. P-4 and P-25.
Perry and Chilton, Chemical Engineer's Handbook, Mcgraw Hill, New York, 1973, pp. 22-24.

Primary Examiner—James C. Housel
Assistant Examiner—Jan M. Ludlow
Attorney, Agent, or Firm—Gaetano D. Maccarone

[57] ABSTRACT

A temperature controlled chamber for an analytical instrument which includes a circular conveyor for transporting assay cartridges, the chamber enclosing the outer peripheral part of the conveyor on which the assay cartridges reside. The temperature controlled chamber has a bottom wall of polymeric material located beneath the conveyor, an outer wall of polymeric material extending upward above the conveyor, a metallic top wall and a metallic inner wall which extends downward to the upper surface of the conveyor. Thermal control, including rapid thermal response to compensate for temperature perturbations induced by periodic introduction of assay cartridges which are at a temperature less than that of the chamber, is accomplished by heating elements located above and below the conveyor. The heating elements are pulsed by an electrical circuit at a rate substantially faster than the rate of introduction of new assay cartridges. Pulses of electric current applied to the heating elements are modulated with pulse-width modulation to adjust the temperature within the chamber in response to signals emitted by a temperature sensor located within the chamber.

11 Claims, 3 Drawing Sheets

TEMPERATURE CONTROLLED CHAMBER FOR DIAGNOSTIC ANALYZER

BACKGROUND OF THE INVENTION

The invention relates to a temperature control system for a temperature controlled chamber in an analytical instrument and, more particularly, to such a system which utilizes heating elements to control the temperature at a predetermined location within the chamber at a desired level.

Various types of chemical tests can be performed by automated test equipment, an example of testing of considerable interest being the assay of biological substances for human health care. Automated test equipment allows large numbers of test samples to be processed rapidly. Such equipment is employed in health care institutions including hospitals and laboratories. Biological fluids, such as whole blood, plasma or serum are tested to find evidence of disease, to monitor therapeutic drug levels, etc.

In the automated test instrument a sample of the test fluid is typically provided in a sample cup and all of the process steps including pipetting of the sample onto an assay test element, incubation and readout of the signal obtained are carried out automatically. The test instrument typically includes a series of work stations each of which performs a specific step in the test procedure. The assay element or cartridge is typically transported from one work station to the next by means of a conveyor such as a carousel to enable the test steps to be accomplished sequentially. The conveyor usually carries a plurality of the assay cartridges, each secured to a specific location on the upper surface of the conveyor. In the usual arrangement, the assay cartridges are spaced apart from each other in berths which are located along the periphery of the conveyor to facilitate automatic insertion and extraction.

In certain types of instruments such as those which are designed to carry out assays based on immunometric interactions between analytes or metabolites and their binding partners, the conveyor carrying the assay elements is arranged within a temperature controlled chamber since it is necessary that the assay be carried out at a very precisely controlled temperature, for example at 37°±0.5° C. The assay elements are maintained in the temperature controlled chamber for a period of time sufficient to bring the assay element to the desired temperature prior to beginning the assay procedure and are maintained at that temperature for the duration of the process.

Various systems for controlling the temperature in such temperature controlled chambers, or incubators, have been disclosed. However, as advances are made in the design of the instruments and, more particularly, in the design and construction of the temperature controlled chambers the known temperature control systems are not entirely satisfactory. For example, consider a temperature controlled chamber which includes a slotted opening in a top wall thereof to permit a pipette to enter the chamber and dispense fluid onto an assay element being carried on a conveyor and which also includes a port in a sidewall to permit the assay elements to be inserted and removed. It is desirable, moreover, to facilitate the manufacture of the chamber and to reduce the cost of the chamber by constructing at least a portion from a moldable polymeric material.

A problem can arise in a temperature controlled chamber of this type which is made at least partly of a polymeric material in the ability to attain the required precision in keeping the temperature at the desired level. This lack of adequate control can be attributed to the poor thermal conductivity of some polymeric materials together with the frequent introduction and removal of assay elements via the port in the sidewall. By way of example, in such instruments new assay elements which are at a temperature less than that of the chamber may be introduced into the chamber at a rate of one assay element every ten seconds over a relatively short period of time. Further, in the case of a chamber constructed at least partly from a polymeric material and which has a single heating element located on the top wall, there has been observed a temperature profile in which the temperature in the vicinity of the bottom wall below the conveyor is several degrees cooler than the temperature in the vicinity of the top wall above the conveyor. In this situation stabilization of the temperature within the chamber could be effected by reducing the rate of entry of new assay elements significantly, for example, one assay element every few minutes. To do so, of course, would reduce the throughput rate of the instrument.

Accordingly, it is an object of this invention to provide a new and improved temperature control system for use in automated analytical instruments which does not require any reduction in the maximum throughput rate which the instrument can otherwise attain.

SUMMARY OF THE INVENTION

These and other objects and advantages are accomplished in accordance with the invention by providing a temperature controlled chamber for an analytical instrument which includes a circular conveyor for transporting assay cartridges, the chamber enclosing the outerperipheral part of the conveyor on which the assay cartridges reside. The temperature controlled chamber comprises a bottom wall of polymeric material located beneath the conveyor, an outer sidewall of polymeric material extending upward above the conveyor, a metallic top wall and a metallic inner sidewall which extends downward to the upper surface of the conveyor. A shaft extends from a conveyor drive mechanism upward through an aperture in the bottom wall to support the conveyor and to impart rotation to the conveyor. The aperture in the bottom wall is sufficiently small to provide no more than a clearance space around the shaft so that the wall can serve as a baffle to prevent a flow of air between the interior space of the chamber and the external environment. Also, an airlock is provided at the junction of the inner wall and a top surface of the conveyor to prevent a flow of air between the interior space of the chamber and the external environment. A port is provided in the outer sidewall for entry and egress of the assay cartridges, and in a preferred embodiment a slotted opening is provided in the top wall to allow for entry of a pipette to dispense fluid to the assay cartridges while they are being transported within the chamber.

In order to increase the thermal dynamic response of the chamber to accomplish a more rapid stabilization of chamber temperature, the volume of an upper region of the chamber is minimized by spacing the inner and the outer sidewalls apart, along the radial dimension of the conveyor, by a distance commensurate with the length of a cartridge, the cartridges being arranged in side-byside relationship along a peripheral region of the conveyor. Also the height of the top wall above the conveyor is sufficiently small to accommodate only the environmental sensors, the assay cartridges, and a clearance space between the sensors and the cartridges.

The heating elements are arranged above and below the conveyor and are energized with pulses of electric current applied at a rate substantially faster and preferably at least double the rate at which new assay cartridges are inserted through the port into the chamber. In response to signals of a temperature sensor, the duration of the pulses is increased or decreased by pulse-width modulation, respectively, to raise or to lower the chamber temperature. It will be appreciated by those skilled in the art that there may exist a temperature gradient across the vertical dimension of the chamber with the areas closest to the top and bottom walls, respectively, being at higher temperatures than the areas more distant from such walls. Such a temperature gradient can be tolerated in the temperature controlled chamber since the critical requirement is that the temperature in the vicinity of the conveyor, including the plane in which the assay cartridges are disposed, has to be controlled within the desired temperature range, e.g., 37°±0.5°C. Thus, a microprocessor may be programmed to receive readings from a temperature sensor located at an area of the chamber which is at a temperature outside the range desired for the assay cartridges and to energize the heaters at a rate which is effective to maintain the assay cartridges within the desired range.

The bottom wall and the outer sidewall of the chamber are constructed of polymeric material. To maximize the rate of heat transfer between the heaters and the interior regions of the chamber, the bottom heater is mounted on the chamber floor directly beneath the conveyor. The top wall and the inner sidewall are constructed of a thermally conductive material, namely, a metal, and the top heater is mounted on the metal top wall.

BRIEF DESCRIPTION OF THE DRAWINGS

For a better understanding of the invention as well as other objects and further features thereof, reference is made to the following detailed description of various preferred embodiments thereof taken in conjunction with the accompanying drawings wherein.

DESCRIPTION OF THE PREFERRED EMBODIMENTS

Figure 1:
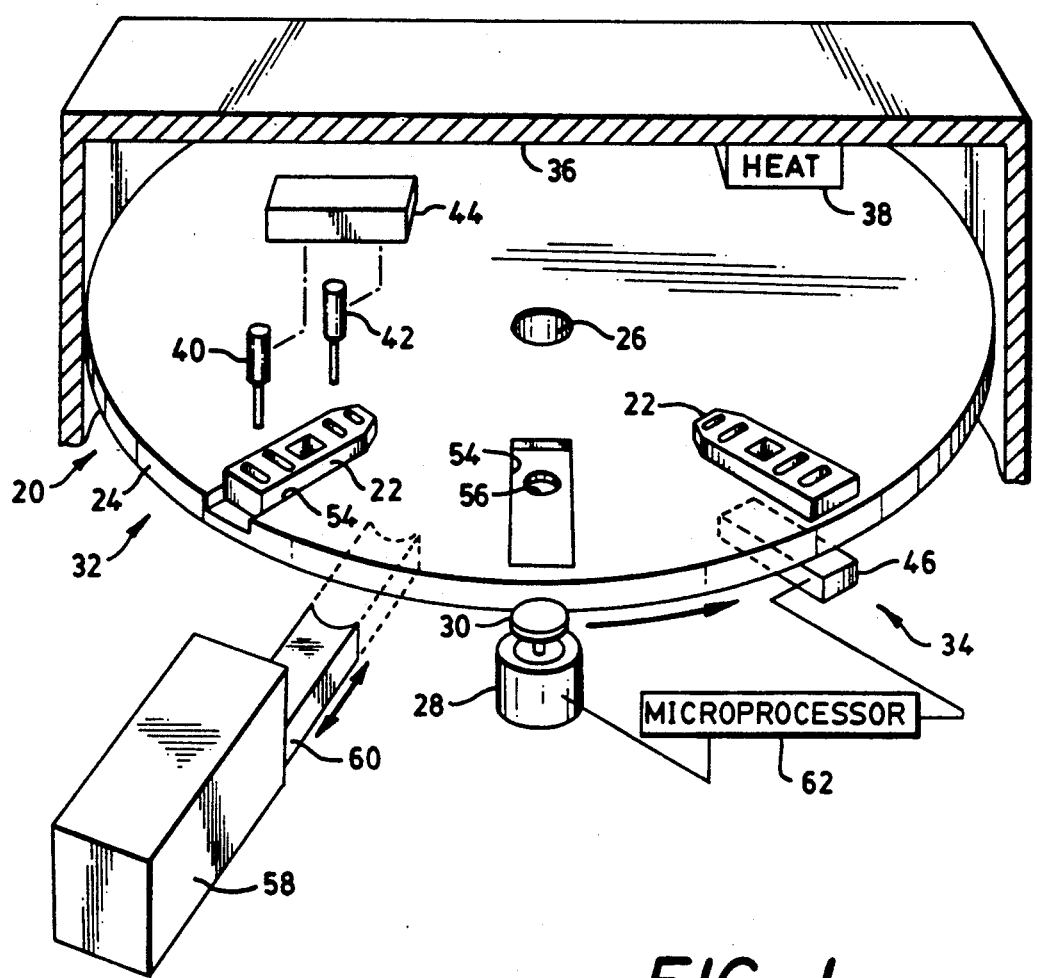
FIG. 1 is a stylized view, partially diagrammatic, of an analytical instrument employing a circular conveyor for moving assay cartridges among various work stations.

In FIG. 1, there is shown an analytical instrument 20 which provides automatically a sequence of process steps to accomplish an assay of a test sample. A plurality of cartridges 22 are employed within the instrument 20 to increase the throughput rate, one process step being carried out with one cartridge concurrently with the performance of other process steps with other cartridges. The cartridges 22 are illustrated with respect to a preferred embodiment thereof which includes one or more chambers in the housing. Such chambers may be configured as wells, or reservoirs, for the storage and/or mixing of fluids which are used in the assay procedure or the chambers may culminate in an opening to permit fluids to be provided to a reaction zone within the cartridge. The chambers are formed integrally within the housing of the cartridge. The analytical instrument 20 includes a conveyor, or carousel, 24, which is rotated about an axle 26 by a motor 28. By way of example, the motor 28 may be mechanically coupled to the carousel 24 by a gear 30 or by a belt drive (not shown). The carousel 24 carries the cartridges 22 from one work station to another work station, two such work stations 32 and 34 being shown, by way of example, in FIG. 1. The carousel 24 rotates within a temperature controlled chamber 36 having a heater 38 for maintaining a desired temperature at the various work stations so as to allow for a process step of incubation.

Work station 32 is a pipetting station whereat sample fluid and any other required fluid test reagent(s) are delivered to the assay cartridges 22. By way of example, there are shown two pipettes 40 and 42. The pipettes, 40 and 42, are positioned and operated by a pipette mechanism 44 mechanically connected to the pipettes 40 and 42, as indicated by dashed lines.

During the assay procedure, as a result of the reaction(s) and interaction(s) between the sample fluid and the test reagent(s) which take place, a detectable change is effected corresponding to the presence of an analyte or component of interest in the sample fluid. The detectable change may be a color change which may be read spectrophotometrically such as with a densitometer or, in an assay method based on fluorescent-labeled biologically active species or one which involves the generation of a fluorescent species as a result of a reaction between test reagents, a fluorescent output signal can be generated and read spectrofluorometrically. Such detectable changes may be read from above or below the assay cartridge. At work station 34 there is shown by way of example a fluorometer 46 for irradiating the reaction zone within the assay cartridge and for measuring the fluorescence emitted from the fluorescent species present therein.

The carousel 24 may be arranged so as to accommodate varying numbers of assay cartridges 22. Each position, or berth 54 for holding an assay cartridge is provided in this embodiment with a small aperture 56 to allow the irradiating illumination to reach the reaction zone in the assay cartridge and to permit the reflected fluorescent emissions to be collected and measured. Also shown in an injector 58 for inserting a cartridge 22 in an empty berth 54, the injector 58 having an arm 60 for gripping a cartridge 22 during the insertion operation. The injector 58 also serves to extract a cartridge from a berth 54 by use of the arm 60 upon completion of a test procedure. Operation of the motor 28, the pipette mechanism 44, the fluorometer 46 and the injector 58 are synchronized by means of a microprocessor unit 62.

Figure 2:
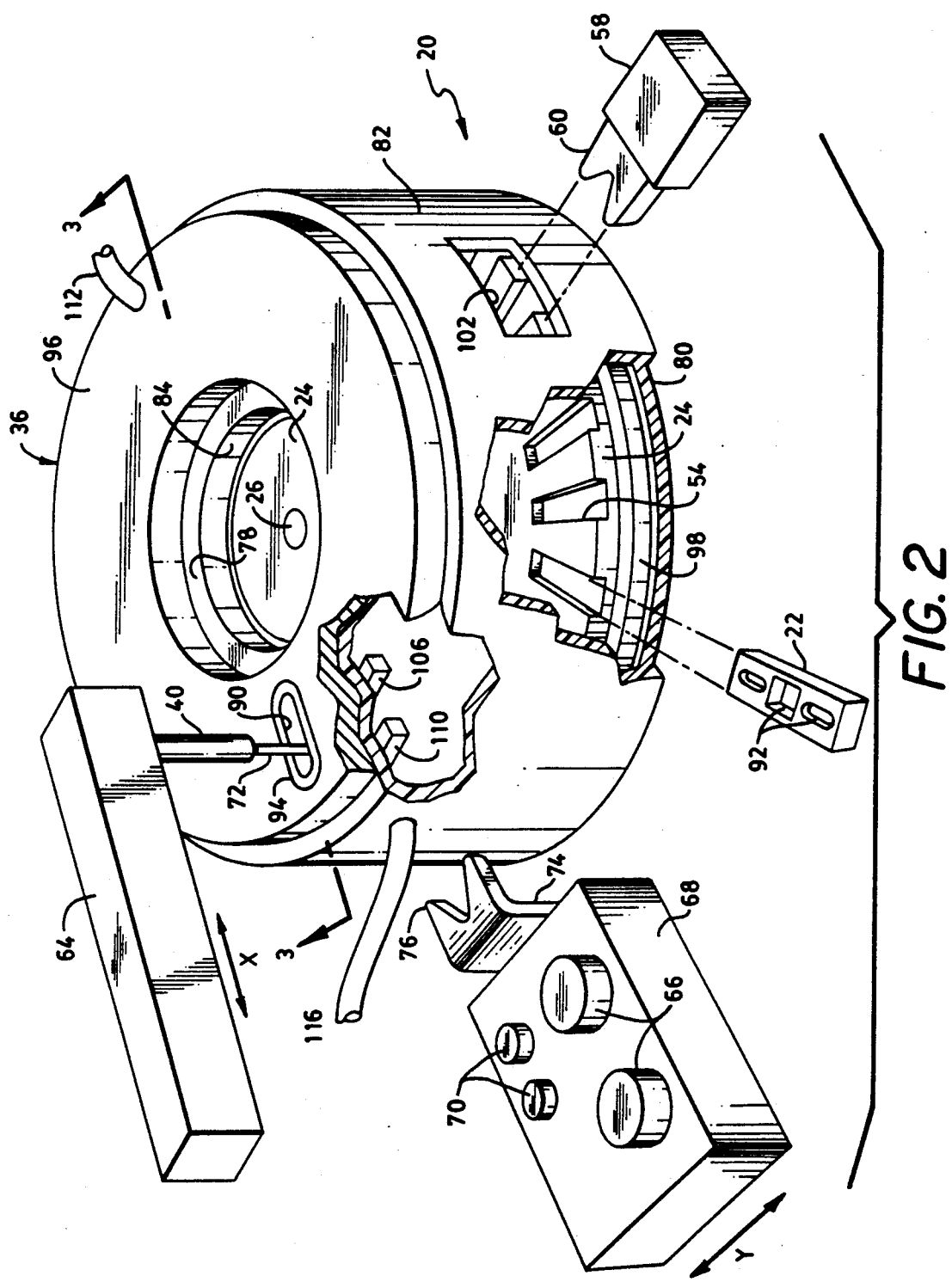
FIG. 2 is a further view of the analytical instrument of FIG. 1 with portions of the instrument indicated diagrammatically, FIG. 2 including a perspective view of a temperature controlled chamber according to the invention with portions of the chamber shown cut away to disclose interior components thereof.
Figure 3:
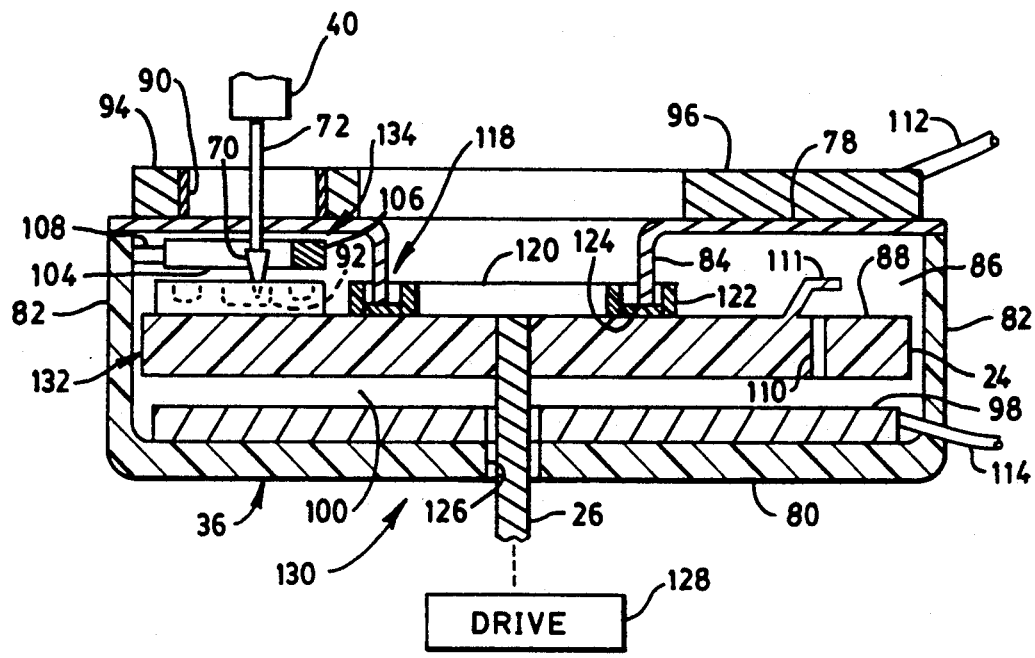
FIG. 3 is a sectional view of the temperature controlled chamber taken along the line 3—3 of FIG. 2.

Referring now to FIG. 2 and 3 there is shown a preferred embodiment of a temperature controlled chamber according to the invention and its operation within the analytical instrument 20. This preferred embodiment is operative with only a single pipette, for example, the pipette 40. The pipette mechanism 44 comprises a transport 64 for moving the pipette 40 in a radial direction (X) of the chamber 36 between the chamber 36 and a selectable reservoir 66 of a plurality of reservoirs 66. The reservoirs 66 are carried upon a table 68 which may be translated in a direction (Y) perpendicular to the pipette movement, X, of the transport 64 so as to enable two axes (X and Y) selection of a reservoir 66 containing a desired fluid. Motorized drives for the transport 64 and the table 68 are available commercially and, accordingly, need not be described in detail herein. In these types of analytical instruments disposable pipette tips are typically used for the delivery of one fluid only and then discarded so as to avoid contamination which could lead to errors in the assay result. Accordingly, the table 68 carries a supply of tips 70 to be inserted upon a stem 72 of the pipette 40. A tip 70 is attached to the stem 72 with frictional force by pushing the stem 72 down into a tip 70 on the table 68. The tip 70 is extracted from the stem 72 by an extractor 74 located alongside the table 68, the extractor 74 having a hooked flange 76 which envelops the tip 70 to pull off the tip 70 during an upward motion of the tip 70.

In accordance with the invention, the temperature controlled chamber 36 comprises a top wall 78, located above the carousel 24, a bottom wall 80 located below the carousel 24, and two sidewalls wherein one of the sidewalls is an outer wall 82 which extends from the top wall 78 to the bottom wall 80 and the second of the sidewalls is an inner wall 84 which extends from the top wall 78 toward a central portion of the carousel 24. The top wall 82 has an annular shape. An upper region 86 of the chamber 36 is bounded by the top wall 78, the top surface 88 of the carousel 24, the outer sidewall 82 and the inner sidewall 84.

In this preferred embodiment the sample fluid and any other required fluid reagents are dispensed to the assay cartridges 22 while the latter are in the temperature controlled chamber. Accordingly, in order to provide access to the assay cartridges 22 by the pipette 40, a slot 90 is provided in the top wall 78 of the chamber 36. The slot 90 extends in a radial direction of the chamber 36, parallel to the X direction. The slot 90 is located relative to the transport 64 to permit the stem 72 of the pipette 40 to be lowered through the slot 90 selectively above a desired compartment of a plurality of compartments 92 of the assay cartridge 22. The length of the slot 90 is commensurate with the length of the cartridge 22 to permit displacement of the stem 72 in the X direction for alignment with a selected one of the compartments 92. The slot 90 is relatively narrow, and is surrounded by a grommet 94. The slot 90 has a width large enough to clear the stem 72 and the tip 70 mounted on the distal end of the stem 72. With respect to the overall dimension of the chamber 36, the area occupied by the slot 90 is sufficiently small to preclude any significant amount of air flow between the interior and the exterior of the chamber 36. Thereby, the slot 90 has no more than a negligible effect in the control of the temperature of the chamber.

The chamber 36 further comprises two heaters, namely, a top heater 96 supported by the top wall 78, and a bottom heater 98 supported by the bottom wall 80 for controlling the chamber temperature. The bottom heater 98 is located in a lower region 100 of the chamber 36, between the carousel 24 and the bottom wall 80. An injection port 102 is provided in the outer sidewall 82 facing the injector 58 to provide access to the arm 60 for inserting a cartridge 22 in a berth 54 of the carousel 24, and for extracting the cartridge 22 from the berth 54. A frame 104 is located within the upper region 86 for supporting sensors useful in the operation of the temperature control system, one such sensor 106 being provided for sensing the chamber temperature. The frame 104 is secured by a bracket 108 to the outer wall 82. By way of example in the construction of the frame 104, the frame 104 may be constructed as a circuit board for supporting electronic circuitry (not shown in FIG. 3) such as a preamplifier for amplifying electrical signals provided by the sensor 106. Electrical cables 112, 114, and 116 connect respectively with the top heater 96, the bottom heater 98, and the sensors 106 and 110 for connecting these components to circuitry outside of the chamber.

To facilitate maintaining a substantially constant temperature within the chamber 36, it is advisable to minimize any flow of air between the interior of the chamber 36 and the external environment. Accordingly, the inner sidewall 84 meets the top surface 88 of the carousel 24 at an airlock 118 which provides sufficient clearance of space between the inner sidewall 84 and the carousel 24 to allow for relative motion between the carousel 24 and the inner sidewall 84, the clearance space being sufficiently narrow to inhibit flow of air between the interior of the chamber 36 and the external environment. The airlock 118 comprises an inner circular rib 120 and an outer circular rib 122 which are spaced apart radially from each other to form a channel for receiving a lip 124 of the inner sidewall 84. The shaft 26 which supports the carousel 24 passes through an aperture 126 in the bottom wall 80. The aperture 126 provides a clearance space which permits rotation of the shaft 26, the rotation being provided by a drive unit 128. The clearance space of the aperture 126 inhibits the flow of air between the interior of the chamber 136 and the external environment. Thus, the bottom wall 80, in combination with the clearance space of the aperture 126 may be regarded as an airlock 130.

The remaining openings in which air may be exchanged between the interior and exterior of the chamber 36 are the injection port 102 and the pipette slot 90. The port 102 is essentially closed off by the structure of the injector 58 except during passage of a cartridge 22 through the port 102. The slot 90 has dimensions such that no more than a negligible amount of air is interchanged between the interior of the chamber and the external environment. For example, for a carousel 24 having a diameter of about 13 inches, the slot 90 can have a width less than about one-quarter inch and a length less than about 1.3 inches. Also, it is noted that the volume of the lower region 100 is sufficiently small, and a gap 132 between the carousel 24 and the outer wall 82 is sufficiently small as to minimize airflow between the upper region 86 and the lower region 100 of the chamber 36. Also, the volume of the upper region 86 is no larger than necessary to accommodate the physical sizes of the cartridges 22 and the sensor assembly 134 comprising the frame 104 and the sensor 106. Minimizing the interior volume of the upper region 86 increases the dynamic response of a temperature control system 136 and reduces transients in the response of the temperature control system 136 to be described below with reference to FIG. 4. The toroidal shape of the upper region 86 aids in reducing the volume of the upper region 86.

Additionally, to maintain circulation of air from the upper region 86 to the lower region 100 there are provided a plurality of apertures, or vents, in the carousel 24 together with a fin to direct the air through the aperture as the carousel is rotated. One such aperture 110 is shown with the fin 111 for purposes of illustration. In a preferred embodiment eight such apertures, each about $\frac{1}{2}"\times\frac{1}{4}"$, are provided in the carousel. Further, since the carousel may be rotated in either direction it is preferred to arrange half of the fins in each direction to facilitate circulation of air irrespective of the direction of rotation.

Figure 4:
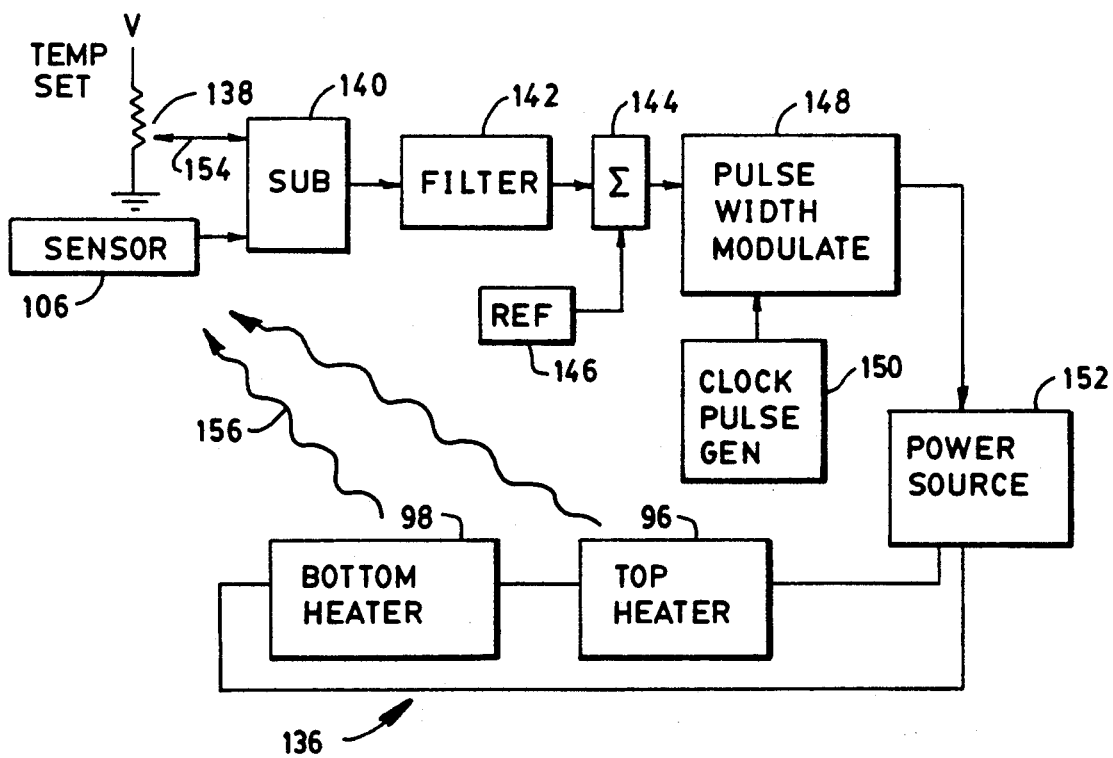
FIG. 4 is a block diagram of a heater control system for energizing top and bottom heaters of the chamber.

In FIG. 4, the temperature control system 136 comprises the temperature sensor 106 and the heaters 96 and 98 disclosed previously in FIG. 3. In addition, the temperature control system 136 comprises a temperature setting potentiometer 138, a subtracter 140, a filter 142, a summer 144, a source 146 of a reference voltage, a pulse width modulator 148, a clock pulse generator 150, and a power source 152.

In operation, the potentiometer 138 is connected between a voltage, V, and ground to provide a manually adjustable output voltage at terminal 154 which is applied to a first terminal of the subtracter 140. An output voltage of the sensor 106 is connected to a second input terminal of the subtracter 140. The subtracter 140 comprises well-known circuitry, such as that of an operational amplifier (not shown), for forming the difference between the voltages of the potentiometer 138 and the sensor 106, and applies the difference to the filter 142. The heaters 96 and 98 are connected serially between output terminals of the power source 152, the source 152 applying electric current to the heaters 96 and 98 for the generation of heat. The heat is indicated symbolically by waves 156 propagating from the heaters 96 and 98 toward the temperature sensor 106.

The power source 152 is gated on and off by pulses provided by the generator 150 via the modulator 148. The voltage reference of the source 146 is applied via the summer 144 to the modulator 148 to establish a basic width to pulses outputted by the modulator 148 to the power source 152. The repetition frequency of the pulses is established by the generator 150. The basic pulse width, in combination with the repetition frequency, establishes a duty cycle for the administration of energizing current to the heaters 96 and 98 which is approximately correct for maintaining a temperature in the desired range, e.g., 37°±0.5° C. in the vicinity of the carousel 24. An output voltage of the filter 142 is applied to the summer 144 to be added algebraically with the reference voltage of the source 146 to adjust the pulse width as needed to increase or decrease the amount of heat produced by the heaters 96 and 98. For example, if the sensor 106, in response to the chamber temperature provided by the heaters 96 and 98, outputs a voltage equal to that of the potentiometer 138, then the error signal outputted by the subtracter 140 is zero, and the modulator 148 outputs pulses at the basic pulse width.

The circuitry of FIG. 4 may be viewed as a feedback loop in which the waves 156 of heat complete the loop by connecting the heaters 96 and 98 to the temperature sensor 106. If the sensor 106 outputs a voltage different from that of the potentiometer 138, a loop error signal outputted by the subtracter 140 has the proper sense, positive or negative, and proper amplitude to adjust the width of the pulses outputted by the modulator 148 for maintaining the desired chamber temperature. For example, if the sensed temperature is too low, the pulse width is increased, and if the sensed temperature is too high, the pulse width is decreased. The filter 142 may be a low-pass filter as is customarily employed in feedback circuitry for precise control of the dynamic response of a feedback loop.

It should be noted here that the system may be controlled entirely by appropriately programming the microprocessor software. In this preferred embodiment the subtractor 140, filter 142, summer 144, source 146, pulse width modulator 148 and clock pulse generator 150 are not necessary.

The main source of interruption of the temperature of the chamber is the insertion of the assay cartridges 22 via the port 102 since the assay cartridges are typically at room temperature which typically is from fifteen to twenty degrees less than that of the chamber. In typical automated analytical instruments the introduction of assay cartridges to the carousel within the chamber can occur at a rate of one every ten seconds, the duration of such rate being dependent, of course, upon the number of open berths 54 on the carousel. Even though a cartridge 22 may be retained within the chamber 36 for a minute or longer prior to beginning the assay procedure in order to stabilize the cartridge temperature, attainment of a desired temperature of the cartridge and of the test material and any reagents contained within the cartridge can only be accomplished adequately by maintaining the chamber temperature in the vicinity of the carousel and the cartridge within the desired range, e.g., 37°±0.5° C. Thus, the perturbations in temperature resulting from the frequent introduction of assay cartridges and removal of the cartridges after the assay procedure has been completed can result in rapid undulations in the chamber temperature which can cause the temperature in the vicinity of the carousel and the assay cartridges to be outside the desired range.

In order to maintain this desired temperature, and to prevent excessive undulations due to the injection of assay cartridges, the pulse repetition frequency provided by the generator 150 is preferably at least double the rate of introduction of assay cartridges, the Nyquist criteria. For example, the current pulses provided by the power source 152 may occur at a repetition frequency of one pulse every three seconds. The average duration of a pulse may be two seconds. This provides a dynamic response to the temperature control system 136 which is adequately fast to deal with the rate of cartridge introduction. The temperature sensor 106 is placed immediately above a plane containing the top surfaces of the cartridges 22 so as to sense the temperature accurately at the openings of the cartridge compartments 92. Also, as has been noted hereinabove, the volume of the upper region 86 is minimized to reduce the amount of air which must be heated, and to reduce the amount of air currents which might otherwise flow about within the chamber 36.

The use of a metallic, thermally conductive, inner sidewall 84 in conjunction with the use of the metallic, thermally-conductive top wall 78 extends a region of heating to a major portion of the upper region 86 for improved thermal response. It is noted that while the bottom wall 80 and the carousel 24 are formed of polymeric material having a relatively low conductivity, there are no openings, such as the injection port 102, in the lower region 100 of the chamber 36 so that the temperature of the lower region can remain stable by the inclusion of the bottom heater 98 in the lower region 100. Therefore, it is possible to construct the bottom wall 80 and the outer sidewall 82 of polymeric material which facilitates and lessens the cost of manufacture, and that only the annular top wall 78 and the cylindrical inner sidewlall 84 need be formed of metal. Any suitable polymeric material may be used for the bottom wall and the outer sidewall such as polyurethane, polycarbonate or the like.

It is understood that the above described embodiment of the invention is illustrative only, and that modifications thereof may occur to those skilled in the art. Accordingly, this invention is not to be regarded as limited to the embodiment disclosed herein, but is to be limited only as defined by the appended claims.

What is claimed is:

1. Apparatus for use in an analytical instrument in which a fluid sample is dispersed to an assay element carried by a circular conveyor and the assay element is analyzed after a period of incubation, said apparatus comprising
   a circular conveyor;
   means defining a temperature controlled chamber extending circumferentially around a peripheral region of said conveyor and extending radially inward partway to the center of said conveyor for enclosing the peripheral region of said conveyor while exposing a central region of said conveyor, said chamber including
   an outer sidewall and an inner sidewall arranged radially inward of said outer sidewall, a top wall spaced above said conveyor and joining said inner and outer sidewalls, first airlock means joining said inner sidewall to said conveyor and second airlock means joining said outer sidewall to said conveyor, said outer sidewall comprising a polymeric material and said top wall and said inner sidewall comprising a thermally conductive material;
   a first heating element located above said conveyor, a second heating element located below said conveyor, and means for pulsing an electric current to said first and second heating elements at a rate sufficient to maintain the temperature adjacent said conveyor within a predetermined range,
   temperature sensing means located within said chamber for sensing the temperature within said chamber
   means for introducing an assay element onto said conveyor through an opening in said housing;
   means for activating said first heating element and said second heating element in response to said temperature sensing means; and
   control means operatively connected to and for controlling said activating means and said introducing means;
   wherein said control means causes said heater activating means to energize said heaters with pulses of electric current at a repetition frequency at least double the rate at which assay elements are introduced onto said conveyor by said introducing means for improved speed of thermal response of said chamber, the duration of said current pulses being modulated by said heater activating means to provide for increased pulse duration for raising the temperature and reduced pulse duration for reducing the temperature.

2. The apparatus as defined in claim 1 wherein said outer sidewall extends from a region above said conveyor past an outer edge of said conveyor to a region below said conveyor, and said second airlock means comprises a bottom wall of polymeric material extending beneath said conveyor and connecting with said outer sidewall.

3. The apparatus as defined in claim 1 wherein said first airlock means comprises a lip formed on a bottom edge of said inner sidewall and channel means located on a top surface of said conveyor, said channel means enveloping said lip.

4. The apparatus as defined in claim 3 wherein said inner sidewall extends from a region above said conveyor past an outer edge of said conveyor to a region below said conveyor, and said second airlock means comprises a bottom wall extending beneath said conveyor and connecting with said outer wall.

5. The apparatus as defined in claim 1 wherein the peripheral region of said conveyor which is enclosed by said chamber includes at least one aperture, each said aperture having in association therewith means for directing a flow of air through said aperture.

6. The apparatus as defined in claim 5 wherein said second airlock means comprises a bottom wall of polymeric material extending beneath said conveyor and connecting with said outer sidewall and said bottom wall is provided with an aperture for allowing passage of a mounting shaft through said bottom wall to said conveyor for imparting relative motion between said conveyor and said chamber.

7. The apparatus as defined in claim 6 wherein said chamber further comprises:
   a radially extending slot disposed in said top wall.

8. The apparatus as defined in claim 7 wherein said first heating element is disposed on said top wall and said second heating element is disposed on said bottom wall.

9. The apparatus as defined in claim 8 wherein said first heating element is coextensive with said top wall and said second heating element is coextensive with said bottom wall.

10. The apparatus as defined in claim 9 wherein said thermally conductive material is a metal, and said means for introducing an assay element is located in said outer wall.

11. The apparatus as defined in claim 10 wherein said conveyor is configured for holding a plurality of assay elements disposed side-by-side along said peripheral region of said conveyor and within said chamber, said outer sidewall being spaced apart from said outer periphery of said conveyor by a clearance spacing and said temperature sensing means being located above said conveyor.

* * * * *